United States Patent
Maldonado et al.

(10) Patent No.: US 11,224,645 B2
(45) Date of Patent: Jan. 18, 2022

(54) GLYCOCONJUGATE VACCINE FOR LEISHMANIASIS

(71) Applicants: Rosa Maldonado, El Paso, TX (US); Igor Almeida, El Paso, TX (US); Katja Michael, El Paso, TX (US); Eva Adriana Iniguez, El Paso, TX (US)

(72) Inventors: Rosa Maldonado, El Paso, TX (US); Igor Almeida, El Paso, TX (US); Katja Michael, El Paso, TX (US); Eva Adriana Iniguez, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 98 days.

(21) Appl. No.: 15/555,369

(22) PCT Filed: Mar. 22, 2016

(86) PCT No.: PCT/US2016/023617
§ 371 (c)(1),
(2) Date: Sep. 1, 2017

(87) PCT Pub. No.: WO2016/160429
PCT Pub. Date: Oct. 6, 2016

(65) Prior Publication Data
US 2018/0043002 A1 Feb. 15, 2018

Related U.S. Application Data

(60) Provisional application No. 62/136,993, filed on Mar. 23, 2015.

(51) Int. Cl.
| | | |
|---|---|---|
| *A61K 39/008* | (2006.01) | |
| *A61K 47/64* | (2017.01) | |
| *A61K 39/00* | (2006.01) | |
| *A61K 39/385* | (2006.01) | |

(52) U.S. Cl.
CPC .......... *A61K 39/008* (2013.01); *A61K 39/385* (2013.01); *A61K 47/643* (2017.08); *A61K 47/646* (2017.08); *A61K 47/6415* (2017.08); *A61K 2039/545* (2013.01); *A61K 2039/6037* (2013.01); *A61K 2039/6081* (2013.01); *Y02A 50/30* (2018.01)

(58) Field of Classification Search
CPC ...... A61K 2039/545; A61K 2039/6037; A61K 39/008; A61K 39/385; A61K 2039/6081; A61K 47/48261; A61K 47/48284; A61K 47/4833; A61K 47/6415; A61K 47/643; A61K 47/646; Y02A 50/41
See application file for complete search history.

(56) References Cited

U.S. PATENT DOCUMENTS

2011/0250196 A1* 10/2011 Barranco ................ A61P 35/00
424/133.1

FOREIGN PATENT DOCUMENTS

| WO | WO 00/34296 | * 6/2000 |
|---|---|---|
| WO | WO/00/034296 | 6/2000 |
| WO | WO/09/146362 | 12/2009 |
| WO | WO/13/178236 | 12/2013 |

OTHER PUBLICATIONS

Kwame et al. Arch. Biochem. Biophys. 426: 182-200, 2004.*
Nikolaev et al. Arch. Biochem. Biophys. 426: 182-200, pp. 1-19, 2004.*
Ashmus RA. Synthesis and conjugation of terminal alpha-Galactose containing. Open Access Theses & Dissertations, University of Texas at El Paso, pp. 1-90, 2010.*
Weislander et al. Glycoconjugate J. 7: 85-100, 1990.*
Almeida et al., *Biochem. J.* 304:793-802, 1994.
Almeida et al., "A highly sensitive and specific chemiluminescent enzyme-linked immunosorbent assay for diagnosis of active Trypanosoma cruzi infection." *Transfusion* 37:850-57, 1997.
Al-Salem, et al., "Detection of high levels of anti-alpha-galactosyl antibodies in sera of patients with Old World cutaneous leishmaniasis: a possible tool for diagnosis and biomarker for cure in an elimination setting" Parasitology. 141:1898-1903, 2014.
Alvar et al., PloS one 7:e35671, 2012.
Ameen, "Cutaneous leishmaniasis: advances in disease pathogenesis, diagnostics and therapeutics." *Clinical and experimental dermatology* 35:699-705, 2010.
Anish, et al., "Chemical biology approaches to designed defined carbohydrate vaccines" Chemistry and Biology. 21:38-50, 2014.
Ashmus, et al., "Potential use of synthetic alpha-galactosyl-containing glycotopes of the parasite Trypanosoma cruzi as diagnostic antigens for Chagas disease" Org Biomol Chem. 11:5579-83, 2013.

(Continued)

*Primary Examiner* — Sarvamangala Devi (57) ABSTRACT

Certain embodiments are directed to an immunogenic composition comprising an immunogenic glycoconjugate comprising a glycan having the chemical formula of galactopyranose (Galp)-α(1,2)-R, Galp-α(1,3)-R, Galp-α(1,4)-R, or Galp-α(1,6)-R, wherein in R is any monosaccharide, oligosaccharide, or polysaccharide, coupled to a carrier peptide or protein. Certain aspects described herein are directed to compounds and therapies for treating *Leishmania* infections. In certain aspects, the glycoconjugates as described herein, are incorporated into pharmaceutical compositions or vaccines

15 Claims, 7 Drawing Sheets
Specification includes a Sequence Listing.

(56) References Cited

OTHER PUBLICATIONS

Avila et al., "Immunogenic Gal alpha 1—3Gal carbohydrate epitopes are present on pathogenic American Trypanosoma and Leishmania." *J Immunol* 142:2828-34, 1989.
Avila et al., *Journal of clinical microbiology* 26:126-132, 1988.
Avila et al., *Journal of clinical microbiology* 26:1842-47, 1988.
Berman, "Human leishmaniasis: clinical, diagnostic, and chemotherapeutic developments in the last 10 years." *Clinical Infectious Diseases.* 24(4):684-703, 1997.
Berman, "Chemotherapy of leishmaniasis: recent advances in the treatment of visceral disease." *Current Opinion in Infectious Diseases.* 11(6): 707-710, 1998.
Completo et al., "Synthesis of galactofuranose-containing acceptor substrates for mycobacterial galactofuranosyltransferases." *J Org Chem.* 73(12):4513-25, 2008.
Croft et al., "Chemotherapy of trypanosomiases and leishmaniasis." *Trends in parasitology* 21:508-12, 2005.
De Assis et al., "Glycoconjugates in New World species of Leishmania: polymorphisms in lipophosphoglycan and glycoinositolphospholipids and interaction with hosts." *Biochimica et biophysica acta* 1820:1354-65, 2012.
Imamura et al., "Extended applications of di-tert-butylsilylene-directed alpha-predominant galactosylation compatible with C2-participating groups toward the assembly of various glycosides." *Chem. Eur. J.* 12:8862-70, 2006.
International Preliminary Report on Patentability in International Application No. PCT/US2016/023617 dated Oct. 5, 2017.
International Search Report and Written Opinion in International Application No. PCT/US2016/023617 dated Jun. 30, 2016.
Launois et al., "Cutaneous leishmaniasis: progress towards a vaccine." *Expert review of vaccines* 7:1277-87, 2008.
McConville and Ferguson, *Biochem J* 294(2):305-24, 1993.
McConville et al., *The Journal of biological chemistry* 265:7385-94, 1990.
McConville et al., *The Journal of biological chemistry* 268:15595-604, 1993.
Mutiso et al., *Journal of biomedical research* 27:85-102, 2013.
Serna et al., *Vaccine* 32:3525-32, 2014.
Tearle et al., "The alpha-1,3-galactosyltransferase knockout mouse. Implications for xenotransplantation." *Transplantation* 61:13-19, 1996.
Wortmann et al., "Rapid identification of Leishmania complexes by a real-time PCR assay." *The American journal of tropical medicine and hygiene* 73:999-1004, 2005.

\* cited by examiner

GLYCOCONJUGATE VACCINE FOR LEISHMANIASIS

CROSS-REFERENCE TO RELATED APPLICATIONS

This application is a national phase application under 35 U.S.C. § 371 of International Application No. PCT/US2016/023617, filed Mar. 22, 2016, which claims priority to U.S. Provisional Application No. 62/136,993 filed on Mar. 23, 2015, which is incorporated herein by reference in its entirety. Both applications are hereby incorporated by reference in their entirety.

BACKGROUND

Leishmaniasis is a vector borne disease that affects 88 countries worldwide. It is also an emerging disease in the U.S. and a growing health concern to the U.S. Army, due to frequent infection of troops deployed to endemic countries in the Middle East. The causal agent is a parasitic protozoon, *Leishmania* ssp. (Alvar et al., PloS one 7:e35671, 2012). Cutaneous leishmaniasis (CL), caused by *L. major, L. mexicana,* and other species, is one of the most important neglected tropical disease and collectively affects up to 1-2 million people. The treatments of choice are highly toxic, and resistance to these drugs has been reported.

Therapies against human leishmaniasis include pentavalent antimonials (sodium stibogluconate and meglumine antimoniate) and amphotericin B (Berman, *Clinical Infectious Diseases.* 24(4):684-703, 1997; Berman, *Current Opinion in Infectious Diseases.* 11(6): 707-710, 1998). Paromomycin, an aminoglycoside, has also shown anti-*Leishmania* activity, but few patients have been treated and the efficacy has been variable in different areas of the world where it was studied (Berman, *Current Opinion in Infectious Diseases.* 11(6):707-710, 1998). These drugs have several disadvantages: (1) their cost is prohibitively high; (2) they are unavailable for oral administration (some of them like amphotericin B can only be used intravenously); and/or (3) they may cause serious side effects that require close monitoring of the patients (Berman, *Clinical Infectious Diseases.* 24(4):684-703, 1997).

There is a need for additional compositions and therapies for treating Leishmaniasis.

SUMMARY

Glycolipids of the various parasite plasma membranes contain terminal α-Galactopyranosyl (α-Galp or, simply, α-Gal) epitopes, which are highly immunogenic to humans. Therefore, patients with cutaneous leishmaniasis (CL) and visceral leishmaniasis (VL) show high levels of anti-α-Gal antibodies (Al-Salem et al., *Parasitology*, 1-6, 2014; Avila et al., *J Immunol* 142:2828-34, 1989; Avila et al., *Journal of clinical microbiology* 26:1842-47, 1988; Avila et al., *Journal of clinical microbiology* 26:126-132, 1988; McConville et al., *The Journal of biological chemistry*, 265:7385-94, 1990). Recently, it has been proposed to use anti-α-Gal antibodies as a biomarker for detection and follow up of treated CL patients (Al-Salem et al., *Parasitology*, 1-6, 2014). Preliminary studies show that α1,3-galactosyltransferase-knockout (α1,3GalT-KO) mice immunized with a synthetic α-Gal-containing neoglycoprotein (αGal-NGP) are partially protected against *L. major* infection. Certain embodiments of the invention described herein are directed to a glycoconjugate vaccine to prevent CL. Neoglycopeptides (NGPeps) were synthesized containing *Leishmania*-specific α-Gal glycans conjugated to the tetanus toxoid peptide (TTp), a known helper T cell epitope, or other helper T cell peptides (e.g., OVA peptide). In certain aspects B cell- and T cell-mediated immune responses to these NGPs are assessed in the α1,3-Galactosyltransferase knockout (α1, 3GalT-KO) mice, which closely resemble humans in their humoral response to αGal epitopes. In certain aspects the vaccine is against *L. major* infection.

Certain embodiments are directed to NGPeps, also referred to herein as neoglycoconjugates. In certain aspects the NGPeps comprises an αGal-containing glycan covalently coupled to a carrier peptide or protein. Certain aspects are directed to an immunogenic composition comprising an immunogenic glycoconjugate or glycan of 2, 3, or more saccharide moieties having a terminal α-galactopyranose (αGalp or αGal) saccharide joined to a second saccharide by an α(1,2), α(1,3), α(1,4), or α(1,6) linkage, which is covalently coupled to a carrier peptide or protein. In a further aspect the NGP is an immunogenic glycoconjugate comprising a glycan having the chemical formula of galactopyranose (Galp)-α(1,2)-R, Galp-α(1,3)-R, Galp-α(1,4)-R, or Galp-α(1,6)-R, wherein in R is any monosaccharide, oligosaccharide, or polysaccharide, coupled to a carrier peptide or protein. In one aspect R comprises one or more galactopyranose (Galp), galactofuranose (Galf), galactose, mannose, glucose, or other monosaccharide(s), or any combination thereof. In a further aspect the saccharides are joined by an α(1,2), α(1,3), α(1,4), or α(1,6) linkage. The carrier peptide can be a tetanus toxoid peptide (TTp) or other helper T cell peptide, or the carrier protein can be bovine serum albumin (BSA) or any other carrier protein (e.g., ovalbumin, keyhole limpet hemocyanin-KLH, etc.). In a further aspects the tetanus toxoid peptide has or consists of an amino acid sequence of EQYIKANSKFIGITE (SEQ ID NO:1). In certain aspects the NGP is G2-TTP (GIPL-2-derived Galpα(1, 3)Galfβ coupled to TTP) and/or G3-TTP (GIPL-3-derived Galpα(1,6)Galpα(1,3)Galfβ glycan coupled to TTP). In certain aspects the glycan is coupled to the amino or carboxy terminus of a carrier peptide.

Galactose can exists in both open-chain and cyclic form. The open-chain form has a carbonyl at the end of the chain. Four isomers are cyclic, two of them with a pyranose (six-membered) ring, two with a furanose (five-membered) ring. In the cyclic form there are two anomers, named alpha and beta, since the transition from the open-chain form to the cyclic form involves the creation of a new stereocenter at the site of the open-chain carbonyl. In the beta form, the alcohol group (at the anomeric carbon) is in the equatorial position in regard to the hydroxyl or alcohol group at carbon 6, whereas in the alpha form, the alcohol group (at the anomeric carbon) is in the axial position in regard to the hydroxyl or alcohol group at carbon 6.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Trypanosomatids are a group of kinetoplastid protozoa distinguished by having only a single flagellum. All members are exclusively parasitic, found primarily in insects. A few genera have life cycles involving a secondary host, which may be a vertebrate, invertebrate, or plant. These include several species that cause major diseases in humans. The three major human diseases caused by trypanosomatids are—African trypanosomiasis (Sleeping Sickness, caused by $Trypanosoma$ $brucei$ and transmitted by Tsetse flies), South American trypanosomiasis (Chagas disease, caused by $Trypanosoma$ $cruzi$ and transmitted by triatomine bugs), and leishmaniasis (a set of trypanosomal diseases caused by various species of $Leishmania$ transmitted by sandflies). Certain aspects described herein are directed to compounds and therapies for treating $Leishmania$ infections.

Leishmaniasis has a wide range of clinical symptoms and over 20 species and subspecies of $Leishmania$ can infect humans, causing three different diseases, visceral (VL), cutaneous (CL), or mucocutaneous leishmaniasis (MCL). Approximately 350 million people are at risk in 88 countries around the world (Ameen, $Clinical$ $and$ $experimental$ $dermatology$ 35:699-705, 2010). Current anti-$Leishmania$ drugs show high toxicity and, frequently, marginal efficacy (Launois et al., $Expert$ $review$ $of$ $vaccines$ 7:1277-87, 2008). Moreover, strains resistant to current treatments have been reported and no vaccine is available (Croft et al., $Trends$ $in$ $parasitology$ 21:508-12, 2005; Mutiso et al., $Journal$ $of$ $biomedical$ $research$ 27:85-102, 2013).

Glycoinositolphospholipids (GIPLs) are major molecules on the plasma membrane of all $Leishmania$ spp. (McConville and Ferguson, $Biochem$ $J$ 294(2):305-24, 1993; de Assis et al., $Biochimica$ $et$ $biophysica$ $acta$ 1820:1354-65, 2012). Specifically in $L.$ $major$ (Old World) and $L.$ $mexicana$ (New World), GIPL-2 and GIPL-3 contain terminal α-Gal residues, which are highly immunogenic to humans (Avila et al., $J$ $Immunol$ 142:2828-34, 1989; Avila et al., $Journal$ $of$ $clinical$ $microbiology$ 26:1842-47, 1988; Avila et al., $Journal$ $of$ $clinical$ $microbiology$ 26:126-32, 1988; McConville et al., $The$ $Journal$ $of$ $biological$ $chemistry$ 265:7385-94, 1990). The current invention uses synthetic glycans, derived from these GIPLs and covalently attached to CD4 T cell epitope, as vaccine candidates for CL.

Synthesis of *Leishmania*-specific α-Gal-containing neoglycopeptides. Neoglycopeptides (NGPs) can be synthesized by solid phase peptide synthesis (Chan and White, *Fmoc solid phase peptide synthesis: a practical approach*, (Oxford University Press: Oxford, 2000)). One NGP consists of the disaccharide Galα(1,3)Galfβ derived from glycoinositolphospholipid 2 (GIPL-2), and another NGP contains the trisaccharide Galpα(1,6)Galpα(1,3)Galfβ derived from GIPL-3, both found in *L. major* and *L. mexicana* (McConville et al., *The Journal of biological chemistry*, 265:7385-94, 1990; McConville and Ferguson, *Biochem J*, 294 (Pt 2):305-24, 1993; McConville et al., *The Journal of biological chemistry* 268:15595-604, 1993). These glycans are covalently attached to a CD4+ T cell epitope, e.g., tetanus toxoid peptide (TTP) (FIG. 1). An unglycosylated TTP can also be synthesized as a reference antigen.

Development of a *Leishmania* glycopeptide-based vaccine platform. α1,3-galactosyltransferase-knockout (α1, 3GalT-KO) mice are immunized with synthetic NGPs and evaluated for B cell- and T cell-mediated immune responses.

αGal1,3T-KO mouse model (Tearle et al., *Transplantation* 61:13-19, 1996) is employed because it closely mimics the human humoral response against the highly immunogenic α-Gal epitopes.

Figure 1:
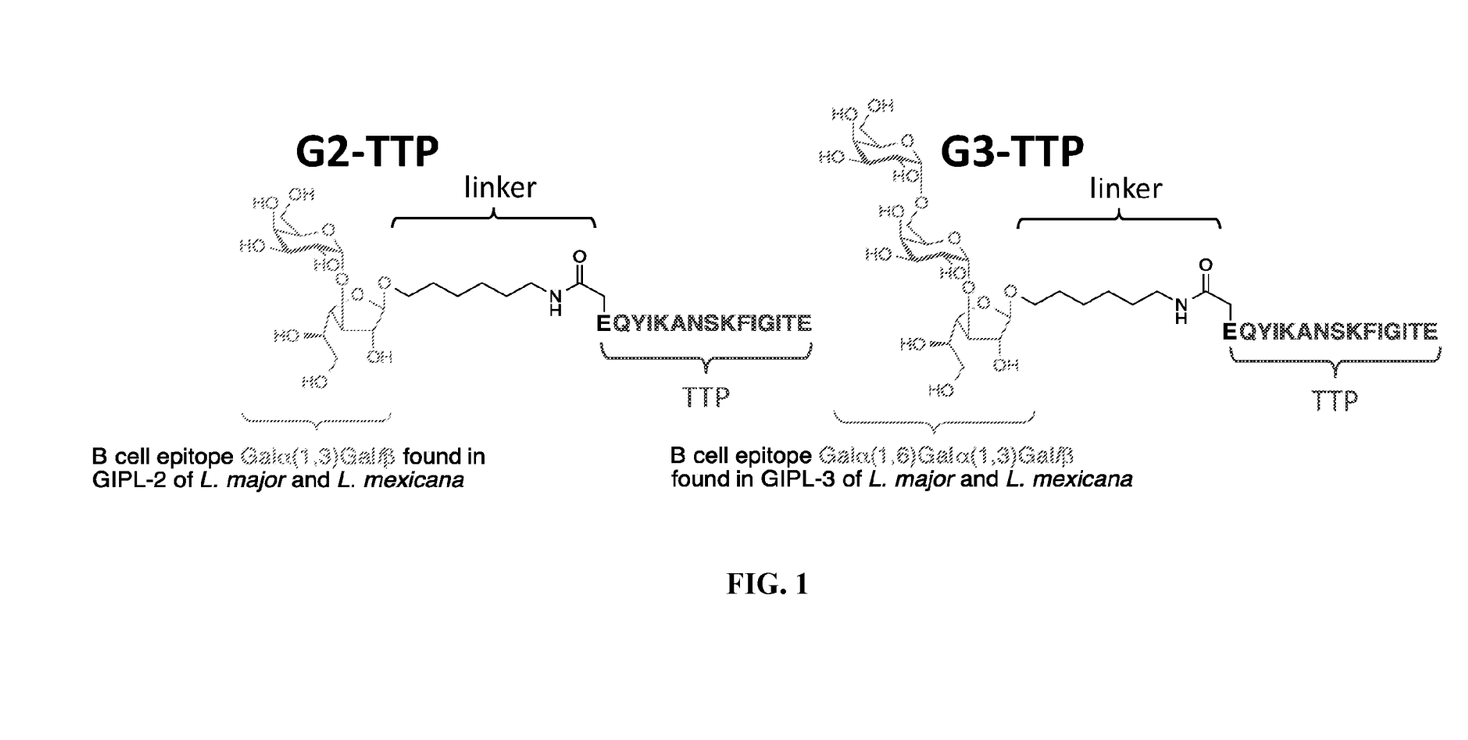
FIG. 1. Schematic representation of two synthetic neoglycopeptides. G2-TTP, GIPL-2-derived Galα(1,3)Galfβ coupled to TTP; and G3-TTP, GIPL-3-derived Galα(1,6) Galα(1,3)Galfβ glycan coupled to TTP. TTP=EQYIKANSKFIGITE (SEQ ID NO:1)
Figure 2:
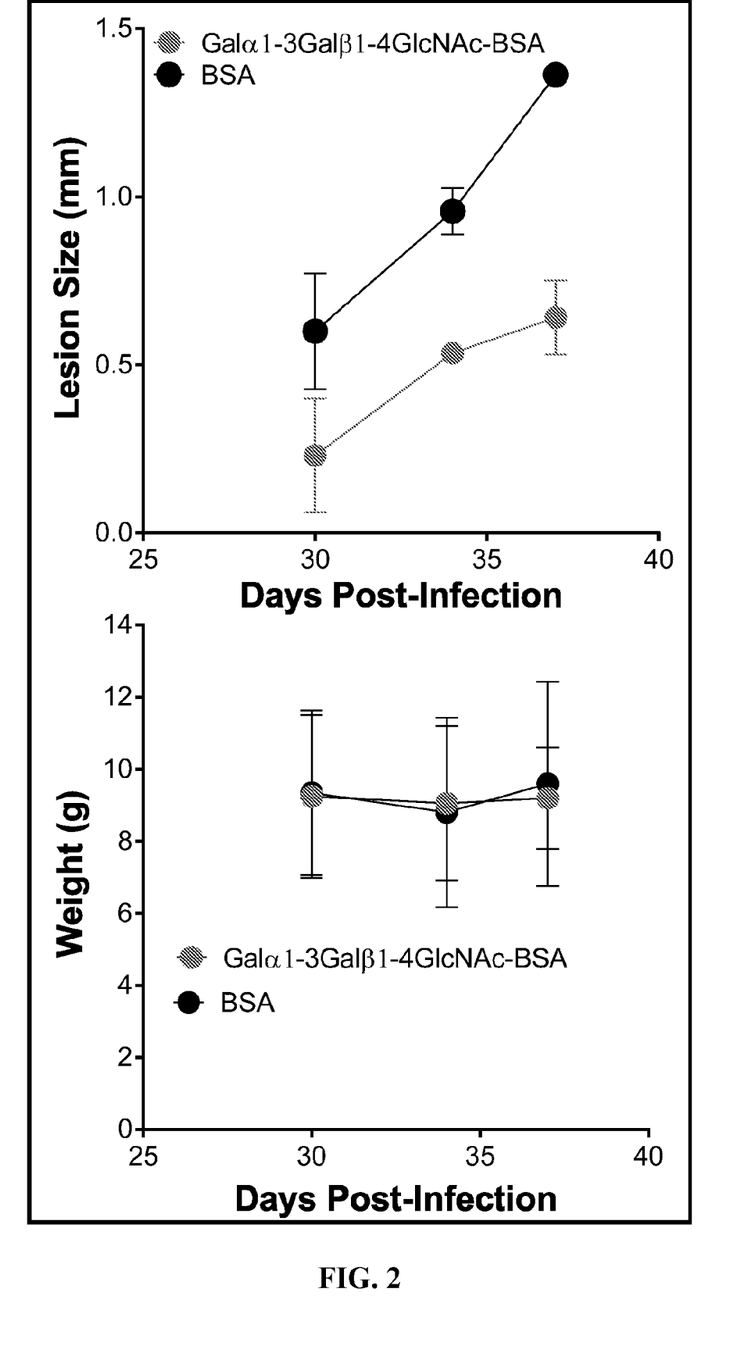
FIG. 2. Immunization of α1,3GalT-KO mice with Galα1, 3Galfβ1,4GlcNAc-BSA (Galα3LN-BSA) induces partial protection against $L.$ $major.$ Lesion in the foot pad was measured with a caliper at days 30, 35, and 37 post-infection.
Figure 3:
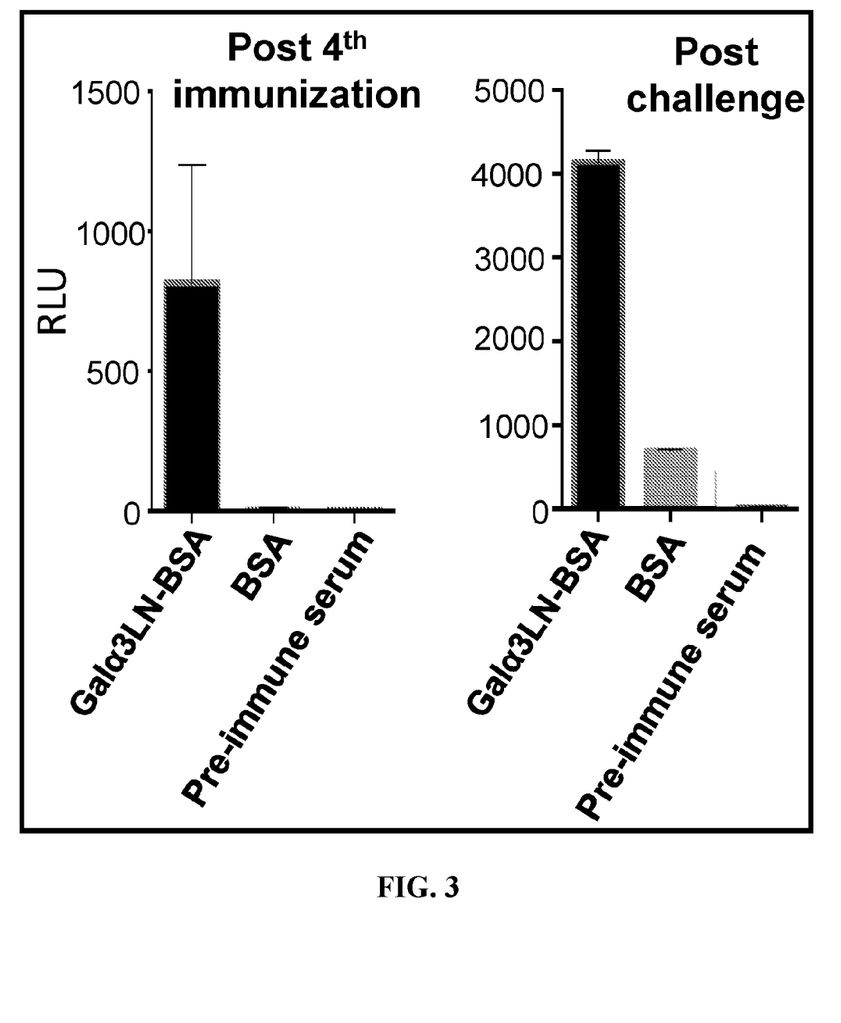
FIG. 3. Anti-α-Gal Ab titers in α1,3GalT-KO mice immunized with Galα3LN-BSA. RLU, relative luminescence units.

Immunization of αGalT-KO mice with Galα1,3Galβ1, 4GlcNAcβ-bovine serum albumin (Galα3LN-BSA) resulted in high levels of anti-α-Gal Abs, accompanied by partial protection from disease (FIG. 2 and FIG. 3) (Tearle et al., Transplantation 61:13-19, 1996). Briefly, α1,3GalT-KO mice (8 weeks old, 5 mice per group) were immunized intraperitoneally (i.p.) four times, at 10-day intervals, with 20 µg Galα3LN-BSA or with BSA (control-placebo). Twelve days after the last immunization, animals were challenged with a lethal dose of $10^6$ *L. major* metacyclic promastigotes. FIG. 2 shows that 37 days post-infection (dpi) immunized mice showed a foot pad lesion 2.3-fold smaller than the control group. Both groups maintained similar weight, suggesting that no toxic effect was caused by the vaccine or placebo. Taken together, these results provide strong evidence of the potential of an α-Gal-based vaccine for CL.

Figure 4:
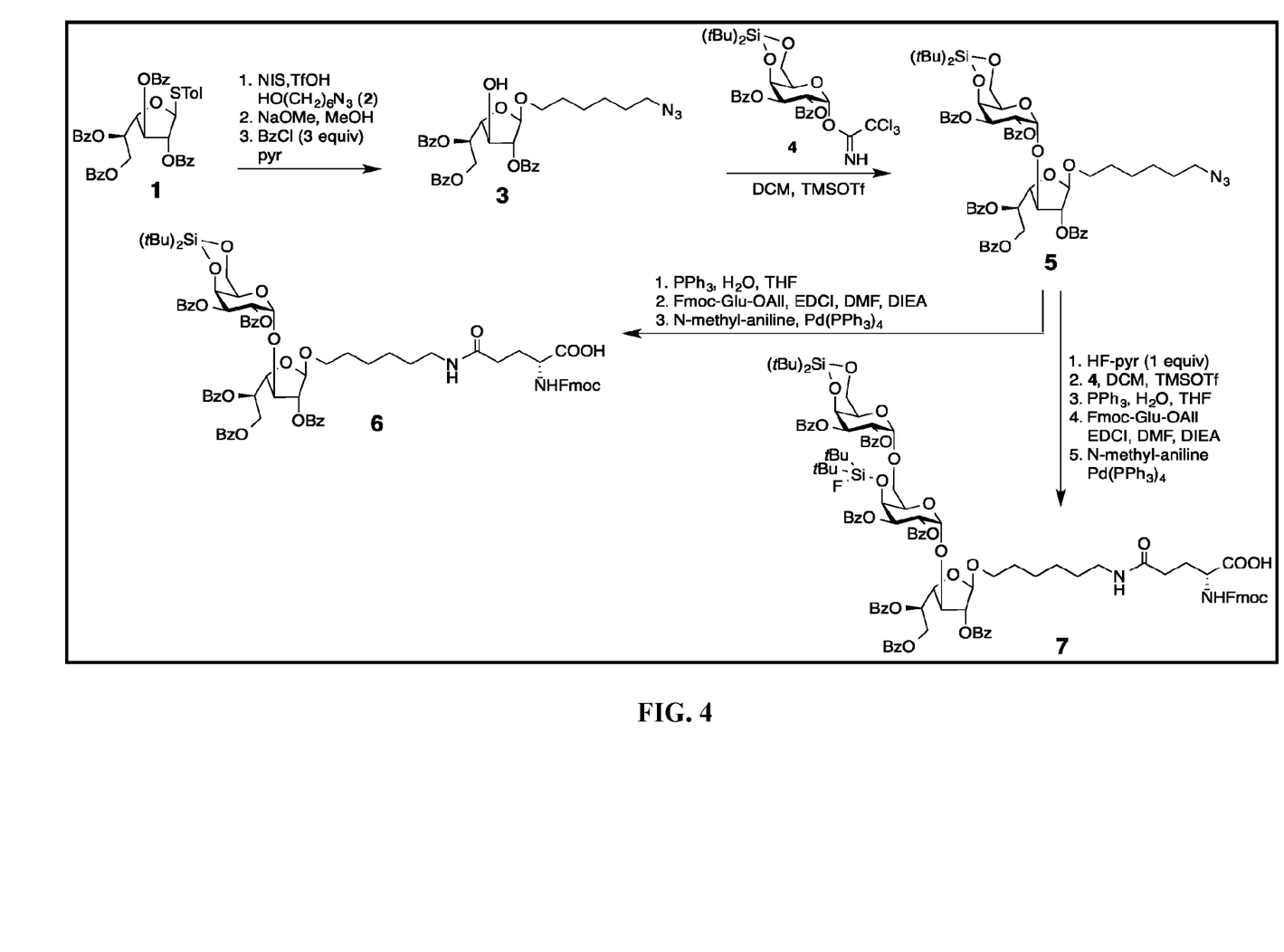
FIG. 4. Synthesis of two glycosyl amino acid building blocks for solid phase peptide synthesis.

Synthesis of two *Leishmania*-specific α-Gal-containing neoglycopeptides. The two glycosyl amino acid building blocks 6 and 7 will be synthesized as shown in FIG. 4 (scheme 1). Galactofuranosyl donor 1 was synthesized following known procedures (Completo and Lowary, *J Org Chem.* 73(12):4513-25, 2008). Glycosylation of linker 2 (Wu et al., *Org. Lett.* 6:4407-10, 2004) followed by removal of the protecting groups and regioselective benzoylation furnishes acceptor 3, which upon α-galactosylation with the galactosyl donor 4 (Kimura et al., *Synlett,* 2379-82, 2006; Imamura et al., *Chem. Eur. J.* 12:8862-70, 2006) produces the fully protected disaccharide 5. Reduction of the azido group by Staudinger reaction, coupling to the amino acid Fmoc-Glu-OAll, and Pd(0)-catalyzed deallylation gives glycosyl amino acid building block 6. Selective ring opening of the DTBS group of compound 5 with HF-pyr complex, followed by glycosylation with donor 4, reduction of the azido group, coupling to the amino acid Fmoc-Glu-OAll and Pd(0)-catalyzed deallylation gives glycosyl amino acid building block 7.

Figure 5:
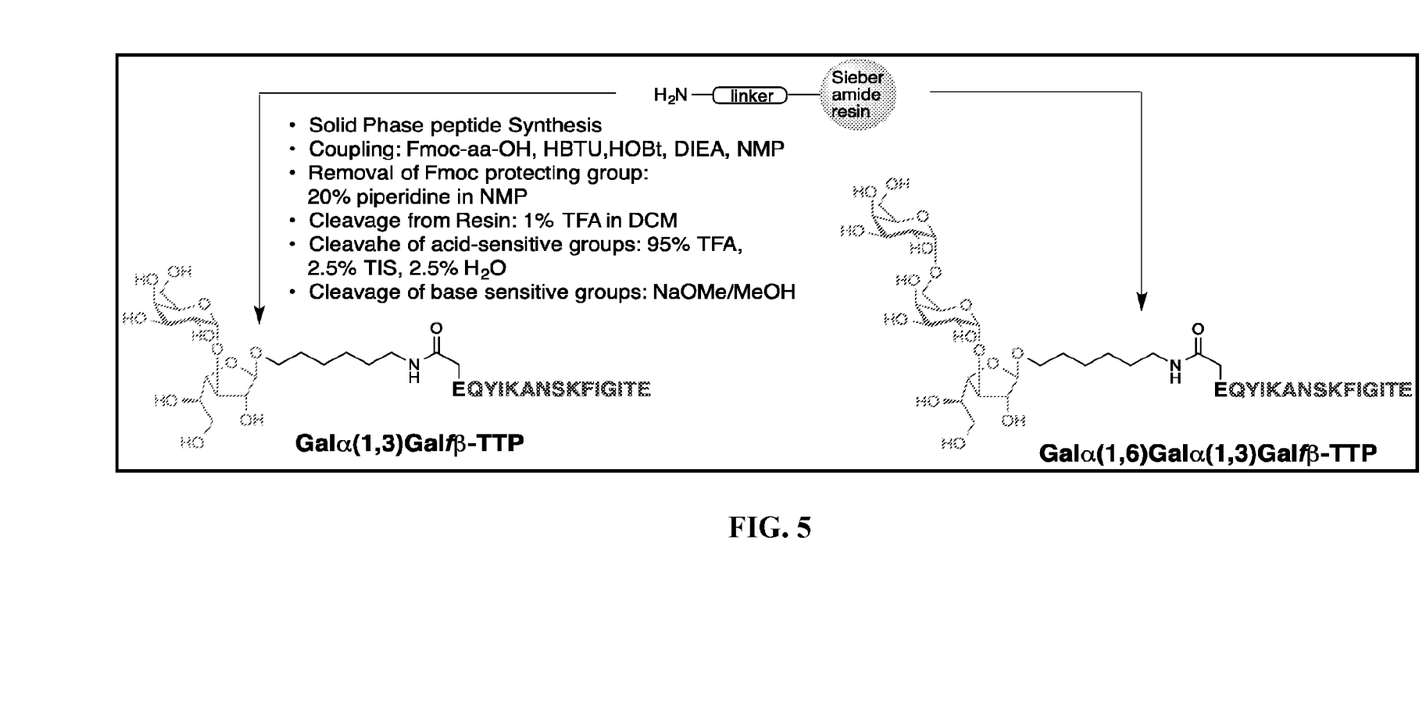
FIG. 5. Solid-phase peptide synthesis of two neoglycopeptides. TTP=EQYIKANSKFIGITE (SEQ NO:1)
Figure 6:
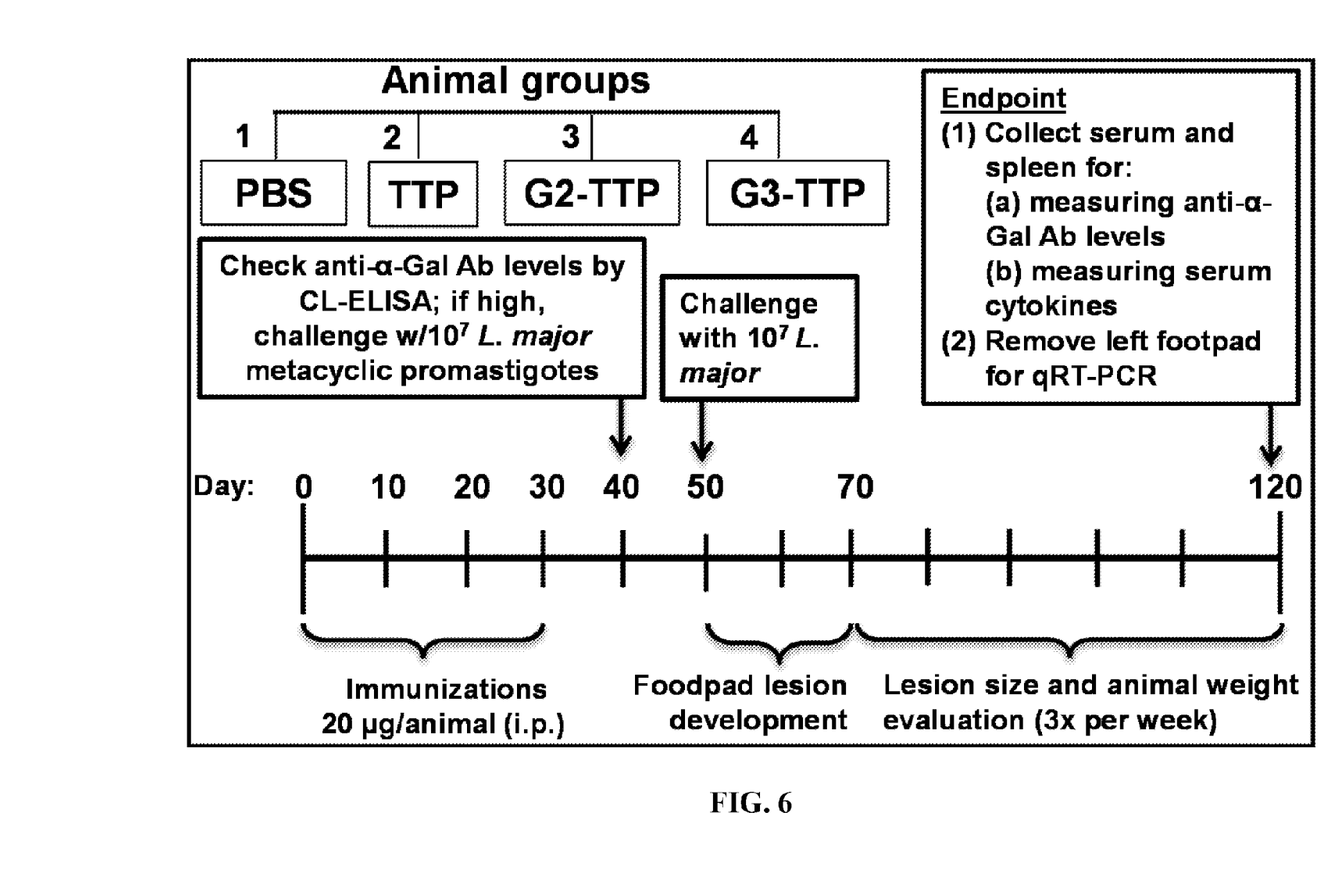
FIG. 6. Vaccination strategy.
Figure 7:
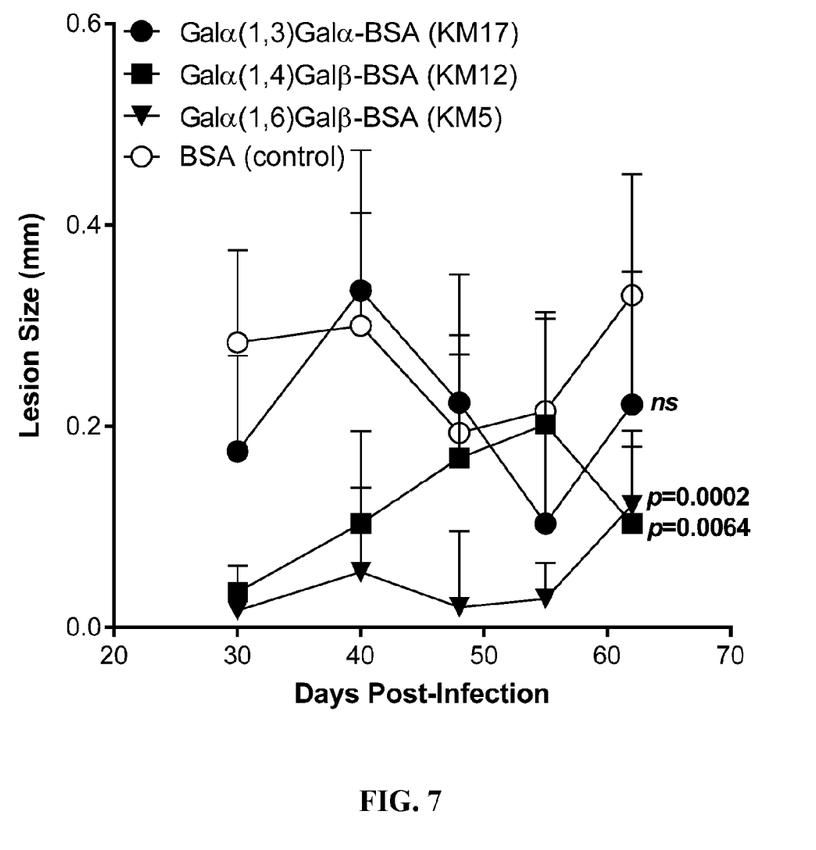
FIG. 7. Immunization of female α1,3GalT-KO mice (C57BL6) (n=6 per group) with the neoglycoprotein (NGP) Galα1,3-Galβ-BSA (KM17), Galα1,4-Galα-BSA (KM12) or Galα1,6-Galβ-BSA (KM5). The immunizations were performed with 10 μg NGP/animal/dose (subcutaneously) at 7-day intervals, in a total of 4 immunizations. Then, the animals were challenged with 1e5 (100,000) $L.$ $major$ (Friedlin strain) metacyclic promastigotes 41 days after the last immunization. Lesion in the foot pad was measured with a caliper at 30, 40, 48, 55 and 62 days post-infection. Statistical analysis: Student's t-test; ns, non-significant.

TTP and the two proposed NGPs, G2 (Galpα(1,3)Galfβ) and G3 (Galpα(1,6)Galpα(1,3)Galfβ) glycan coupled to TTP (G3-TTP) will be synthesized by solid phase peptide synthesis using the Fmoc strategy, Sieber amide resin, and standard coupling conditions (FIG. 5, scheme 2).

Cleavage from the resin is achieved with 1% TFA. The NGPs are purified by silica column and/or size exclusion chromatography. After deprotection of the amino acid side chains with TFA, and removal of the ester groups with sodium methoxide, the neoglycopeptides are chromatographed by reversed phase HPLC, characterized by ESI-TOF-MS, and are ready to be used as immunogens.

*Leishmania* glycopeptide-based vaccine platform. FIG. 6 illustrates a vaccination strategy. Four experimental groups are used to test the NGPs described herein. Briefly, animals (n=10, each group) receive four immunizations of 20 μg G2-TTP (group 3) or G3-TTP (group 4) per animal per dose, with 10-day interval between immunizations. The control groups (n=10, each) receives phosphate-buffered saline (PBS; immunization vehicle) (group 1) or 20 μg TTP (group 2) (FIG. 6). All immunizations are done by intraperitoneal (i.p.) injection (max. vol. 200 μl).

Ten days after the $4^{th}$ immunization (day 30), individual sera from all animal groups is obtained and analyzed for anti-α-Gal Ab titers by CL-ELISA, using G2-TTP and G3-TTP as antigens. Immunoglobulin isotyping is performed, using commercially available kit (BD Pharmingen). All animals are challenged by i.d. injection in the left footpad with $10^7$ infective *L. major* metacyclic promastigotes. The animals are monitored 3× per week. Lesions start to appear 20 dpi. Mice are then monitored 3× per week, the size of the lesion and the animal weight is assessed during 50 days. To assess parasite load in the footpad quantitative real-time PCR (qRT-PCR) is performed at day 120 (experimental endpoint) (Wortmann et al., *The American journal of tropical medicine and hygiene* 73:999-1004, 2005). Upon observation of any abnormal physical appearance (e.g., weight loss, febrile state, distress, etc.), control animals (groups 1 and 2) are humanely euthanized and the footpad harvested for qRT-PCR. Groups 3 and 4 are euthanized at day 120 and the left footpad collected for qRT-PCR analysis. The immunogenicity of both NGPs is evaluated by chemiluminescent-ELISA (Almeida et al., *Transfusion* 37:850-57, 1997) and lytic anti-α-Gal antibody assay (Almeida et al., *Biochem. J.* 304:793-802, 1994), using sera of the immunized mice. Sera from patients with *L. major* infection, which contain high levels of anti-α-Gal Abs, are used as positive controls. The cell-mediated immune response to the two NGPs and controls is evaluated first by measuring the profile of proinflammatory (IFN-γ, TNFα, IL-2, IL-12, and IL-17) and anti-inflammatory/regulatory (IL-4 and IL-10) cytokines in the serum (Sema et al., *Vaccine* 32:3525-32, 2014), and by intracellular cytokine staining (ICS) of spleen cells (ProImmune). These assays are performed before and after challenge with lethal dose of parasites of the immunized mice.

Immunization of female αGal1,3T-KO mice (C57BL6) (n=6 per group) with the neoglycoprotein (NGP) Galα1,3-Galfβ-BSA (KM17), Galα1,4-Galα-BSA (KM12) or Galα1,6-Galβ-BSA (KM5) (FIG. 7). The immunizations were performed with 10 μg NGP/animal/dose (subcutaneously) at 7-day intervals, in a total of 4 immunizations. Then, the animals were challenged with 1000,000 *L. major* (Friedlin strain) metacyclic promastigotes 41 days after the last immunization. Lesion in the foot pad was measured with a caliper at 30, 40, 48, 55 and 62 days post-infection. Statistical analysis: Student's t-test; ns, non-significant.

Pharmaceutical and Vaccine Compositions

In certain aspects, the glycoconjugates as described herein, are incorporated into pharmaceutical compositions or vaccines. Pharmaceutical compositions generally comprise one or more glycoconjugates as described herein in combination with a physiologically acceptable carrier. Vaccines, also referred to as immunogenic compositions, generally comprise one or more of the glycoconjugates as described herein, in combination with an immunostimulant, such as an adjuvant. In particular embodiments, the pharmaceutical compositions comprise glycoconjugates as described herein that are capable of providing protection against, for example in an in vivo assay as described herein, *Leishmania* species such as *L. donovani, L. major,* or *L. infantum.*

An immunostimulant may be any substance that enhances or potentiates an immune response (antibody and/or cell-mediated) to an exogenous antigen. In certain aspects an immunostimulant can be covalently attached and/or co-formulated with an antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this invention. For example, an adjuvant may be included. Many adjuvants contain a substance designed to protect the antigen from rapid catabolism, such as aluminum hydroxide or mineral oil, and a stimulator of immune responses, such as lipid A (natural or synthetic), *Bordatella pertussis* or *Mycobacterium* species or *Mycobacterium*-derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (GlaxoSmithKline Beecham, Philadelphia, Pa.); CWS, TDM, LeIF, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

The vaccine and pharmaceutical compositions of the invention may be formulated using any of a variety of well-known procedures. In certain embodiments, the vaccine or pharmaceutical compositions are prepared as stable emulsions (e.g., oil-in-water emulsions) or as aqueous solutions.

In the compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intradermal, subcutaneous and intramuscular administration and formulation.

In certain applications, the compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In most cases the form must be sterile and must be fluid to the extent that easy syringability exists. It can be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known to one of ordinary skill in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood to one of ordinary skill in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the compositions of the present invention may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosnon-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Glu Gln Tyr Ile Lys Ala Asn Ser Lys Phe Ile Gly Ile Thr Glu
1               5                   10                  15
``` phatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The pharmaceutical compositions and vaccines of the invention may be used, for example, to induce protective immunity against *Leishmania* species such as *L. donovani, L. major* and/or *L. infantum* in a patient, such as a human or a dog, to prevent leishmaniasis or diminish its severity. The compositions and vaccines may also be used to stimulate an immune response, which may be cellular and/or humoral, in a patient, for treating an individual already infected.

Appropriate doses and methods of administration for these purposes can be readily determined by a skilled artisan using available knowledge in the art and/or routine techniques. Routes and frequency of administration, as well as dosage, for the above aspects of the present invention may vary from individual to individual and may parallel those currently being used in immunization against other infections, including protozoan, viral and bacterial infections. For example, in one embodiment, between 1 and 12 doses of composition having glycoconjugate are administered over a 1 year period. Booster vaccinations may be given periodically thereafter as needed or desired. Of course, alternate protocols may be appropriate for individual patients. In a particular embodiment, a suitable dose is an amount of glycoconjugate that, when administered as described above, is capable of eliciting an immune response in an immunized patient sufficient to protect the patient from leishmaniasis caused by *Leishmania* species such as *L. donovani, L. major* and/or *L. infantum* for at least 1-2 years. In general, the amount of glycoconjugate present in a dose ranges from about 100 ng to about 1 mg per kg of host, typically from about 10 μg to about 100 μg. Suitable dose sizes will vary with the size of the patient, but will typically range from about 0.1 mL to about 5 mL.

The various embodiments described above can be combined to provide further embodiments. All of the U.S. patents, U.S. patent application publications, U.S. patent applications, foreign patents, foreign patent applications and

The invention claimed is:

1. An immunogenic glycoconjugate, wherein the immunogenic glycoconjugate is a glycoinositolphospholipid (GIPL)-2-derived Galpα(1,3)Galfβ-tetanus toxoid peptide (TTP) (G2-TTP) glycoconjugate or a GIPL-3-derived Galpα (1,6)Galpα(1,3)Galfβ-TTP glycoconjugate (G3-TTP).

2. The immunogenic glycoconjugate of claim 1, wherein the tetanus toxoid peptide consists of the amino acid sequence of EQYIKANSKFIGITE (SEQ ID NO:1).

3. The immunogenic glycoconjugate of claim 1, wherein the immunogenic glycoconjugate is formulated as a vaccine composition.

4. A method of inducing an immune response in a mammal to comprising administering the immunogenic glycoconjugate of claim 1.

5. The method of claim 4, wherein the immune response is induced in a human or canine.

6. The method of claim 4, wherein the mammal has cutaneous leishmaniasis (CL).

7. The method of claim 4, wherein the immunogenic composition is administered two or more times.

8. A method for treating Leishmaniasis by inducing in a mammal an immune response against Leishmaniasis comprising the step of administering to the mammal a composition comprising the glycoconjugate of claim 1.

9. The method of claim 8, wherein the tetanus toxoid peptide consists of the amino acid sequence of EQYIKANSKFIGITE (SEQ ID NO: 1).

10. The method of claim 8, wherein the mammal is a human or canine.

11. The method of claim 8, wherein the mammal is infected with *Leishmania major* or *Leishmania mexicana*.

12. A glycoconjugate having the chemical formula of
(a) (Galp)α(1,6)(Galp)α(1,3) Galfβ coupled to a carrier protein or a carrier peptide comprising a helper T cell epitope; or
(b) Galpα(1,3)Galfβ disaccharide coupled to a carrier protein or a carrier peptide comprising a helper T cell epitope, wherein carbohydrate portion of the glycoconjugate consists of the disaccharide.

13. The glycoconjugate of claim 12, wherein the carrier peptide is a tetanus toxoid peptide or the carrier protein is bovine serum albumin (BSA).

14. The glycoconjugate of claim 13, wherein the carrier peptide is a tetanus toxoid peptide.

15. The immunogenic glycoconjugate of claim 14, wherein the tetanus toxoid peptide consists of the amino acid sequence of EQYIKANSKFIGITE (SEQ ID NO:1).

* * * * *